(12) United States Patent
Yoon et al.

(10) Patent No.: US 6,214,028 B1
(45) Date of Patent: Apr. 10, 2001

(54) SURGICAL INSTRUMENT WITH MULTIPLE ROTATABLY MOUNTED OFFSET END EFFECTORS AND METHOD OF USING THE SAME

(75) Inventors: InBae Yoon, 2101 Highland Ridge Dr., Phoenix, MD (US) 21131; Samuel C. Yoon, Timonium, MD (US)

(73) Assignee: InBae Yoon, Ellicott City, MD (US)

( * ) Notice: Subject to any disclaimer, the term of this patent is extended or adjusted under 35 U.S.C. 154(b) by 0 days.

(21) Appl. No.: 09/368,574

(22) Filed: Aug. 5, 1999

Related U.S. Application Data

(62) Division of application No. 08/847,189, filed on May 1, 1997, now Pat. No. 6,017,358.

(51) Int. Cl.[7] .................................................. A61B 17/28
(52) U.S. Cl. ........................... 606/205; 606/41; 606/139; 600/564
(58) Field of Search ............................. 606/205–211, 174, 606/1, 41, 32, 45–52; 600/564–567; 128/898

(56) References Cited

U.S. PATENT DOCUMENTS

| | | |
|---|---|---|
| 0,919,138 | 4/1909 | Drake . |
| 1,037,864 | 9/1912 | Carlson . |
| 1,131,163 | 3/1915 | Saudners . |
| 1,155,378 | 10/1915 | Steedman . |
| 1,449,087 | 5/1923 | Bugbee . |
| 1,822,330 | 9/1931 | Ainslie . |
| 2,213,830 | 9/1940 | Anastasi . |
| 2,580,964 | 1/1952 | Skaller . |
| 2,601,564 | 6/1952 | Smith . |
| 2,646,045 | 7/1953 | Priestley . |
| 2,959,172 | 11/1960 | Held . |
| 3,090,386 | 5/1963 | Curtis . |
| 3,139,089 | 6/1964 | Schwerin . |
| 3,349,772 | 10/1967 | Rygg . |
| 3,470,875 | 10/1969 | Johnson . |
| 3,842,840 | 10/1974 | Schweizer . |
| 3,946,740 | 3/1976 | Bassett . |
| 4,109,658 | 8/1978 | Hughes . |

(List continued on next page.)

FOREIGN PATENT DOCUMENTS

WO97/37583    10/1997  (WO) .

*Primary Examiner*—Glenn K. Dawson
(74) *Attorney, Agent, or Firm*—Blank Rome Comisky & McCauley LLP

(57) ABSTRACT

An instrument for operating on anatomical tissue includes a barrel having two or more driver therein which can be manipulated from a proximal end of the barrel. End effectors of each driver are offset from a rotatable shaft by a transverse arm. In an insertion position, the end effectors are confined within the diametrical dimension of the barrel at a distal end thereof. After insertion, the end effectors can be manipulated to extend beyond the diametrical dimension of the barrel to provide a large working span for manipulating tissue or performing other procedures on tissue.

8 Claims, 14 Drawing Sheets

U.S. PATENT DOCUMENTS

| | | | |
|---|---|---|---|
| 4,164,225 | 8/1979 | Johnson . | |
| 4,257,420 | 3/1981 | Terayama . | |
| 4,440,171 | 4/1984 | Nomoto . | |
| 4,557,265 | 12/1985 | Andersson . | |
| 4,621,640 | 11/1986 | Mulhollan . | |
| 4,635,638 | 1/1987 | Weintraub et al. . | |
| 4,935,027 | 6/1990 | Yoon | 606/146 |
| 5,037,433 | 8/1991 | Wilk | 606/139 |
| 5,100,421 | 3/1992 | Christoudias | 606/147 |
| 5,147,373 | 9/1992 | Ferzli | 606/144 |
| 5,181,919 | 1/1993 | Bergman | 606/144 |
| 5,209,741 | 5/1993 | Spaeth | 604/264 |
| 5,211,650 | 5/1993 | Noda | 606/139 |
| 5,222,508 | 6/1993 | Contarini | 128/898 |
| 5,234,443 | 8/1993 | Phan | 606/148 |
| 5,244,948 | 9/1993 | Mulhaupt et al. . | |
| 5,261,917 | 11/1993 | Hasson | 606/139 |
| 5,281,238 | 1/1994 | Chin | 606/148 |
| 5,304,185 | 4/1994 | Taylor | 606/147 |
| 5,305,121 | 4/1994 | Moll | 348/45 |
| 5,308,353 | 5/1994 | Beurrier | 606/144 |
| 5,320,632 | 6/1994 | Heidmueller | 606/144 |
| 5,336,230 | 8/1994 | Leichtling | 606/148 |
| 5,336,231 | 8/1994 | Adair | 606/148 |
| 5,356,424 | 10/1994 | Buzerak | 606/223 |
| 5,364,408 | 11/1994 | Gordon | 606/144 |
| 5,364,409 | 11/1994 | Kuwabara | 606/148 |
| 5,374,275 | 12/1994 | Bradley | 606/144 |
| 5,376,096 | 12/1994 | Foster | 606/147 |
| 5,389,098 | 2/1995 | Tsuruta | 606/41 |
| 5,389,103 | 2/1995 | Melzer | 606/144 |
| 5,395,367 | 3/1995 | Wilk | 606/1 |
| 5,397,325 | 3/1995 | Della Badia | 606/144 |
| 5,403,328 | 4/1995 | Shallman | 606/144 |
| 5,403,329 | 4/1995 | Hinchcliffe | 606/147 |
| 5,437,681 | 8/1995 | Meade | 606/145 |
| 5,454,823 | 10/1995 | Richardson | 606/148 |
| 5,462,561 | 10/1995 | Voda | 606/144 |
| 5,462,562 | 10/1995 | Elkus | 606/148 |
| 5,468,251 | 11/1995 | Buelna | 606/223 |
| 5,470,338 | 11/1995 | Whitfield | 606/144 |
| 5,474,057 | 12/1995 | Makower | 600/214 |
| 5,474,568 | 12/1995 | Scott | 606/144 |
| 5,477,794 | 12/1995 | Klundt . | |
| 5,478,344 | 12/1995 | Stone | 606/144 |
| 5,478,345 | 12/1995 | Stone | 606/144 |
| 5,480,406 | 1/1996 | Nolan | 606/139 |
| 5,496,310 | 3/1996 | Exconde | 606/205 |
| 5,496,334 | 3/1996 | Klundt | 606/145 |
| 5,503,634 | 4/1996 | Christy | 606/144 |
| 5,520,703 | 5/1996 | Essig | 606/148 |
| 5,540,704 | 7/1996 | Gordon | 606/144 |
| 5,540,705 | 7/1996 | Meade | 606/145 |
| 5,545,148 | 8/1996 | Wurster | 604/223 |
| 5,562,640 | 10/1996 | McCabe | 604/280 |
| 5,562,685 | 10/1996 | Mollenauer | 606/144 |
| 5,562,686 | 10/1996 | Sauer | 606/144 |
| 5,562,703 | 10/1996 | Desai | 606/210 |
| 5,569,164 | 10/1996 | Lurz | 600/158 |
| 5,569,269 | 10/1996 | Hart | 606/144 |
| 5,569,270 | 10/1996 | Weng | 606/144 |
| 5,573,542 | 11/1996 | Stevens | 606/144 |
| 5,578,048 | 11/1996 | Pasqualucci | 606/192 |
| 5,582,617 | 12/1996 | Klieman | 606/170 |
| 5,591,181 | 1/1997 | Stone | 606/144 |
| 5,601,575 | 2/1997 | Measamer | 606/147 |
| 5,603,718 | 2/1997 | Xu | 606/145 |
| 5,607,435 | 3/1997 | Sachdeva | 606/139 |
| 5,609,601 | 3/1997 | Kolesa | 606/170 |
| 5,626,588 | 5/1997 | Sauer | 606/144 |
| 5,632,751 | 5/1997 | Piraka | 606/139 |
| 5,632,752 | 5/1997 | Buelna | 606/144 |
| 5,643,292 | 7/1997 | Hart | 606/144 |
| 5,662,663 | 9/1997 | Shallman | 606/144 |
| 5,674,230 | 10/1997 | Tovey | 606/139 |
| 5,702,407 | 12/1997 | Kaji | 606/139 |
| 5,707,379 | 1/1998 | Fleenor | 606/145 |
| 5,709,693 | 1/1998 | Taylor | 606/145 |
| 5,709,694 | 1/1998 | Greenberg | 606/148 |
| 5,713,908 | 2/1998 | Jameel | 606/148 |
| 5,722,990 | 3/1998 | Sugarbaker | 606/207 |
| 5,759,188 * | 6/1998 | Yoon | 606/147 |

* cited by examiner

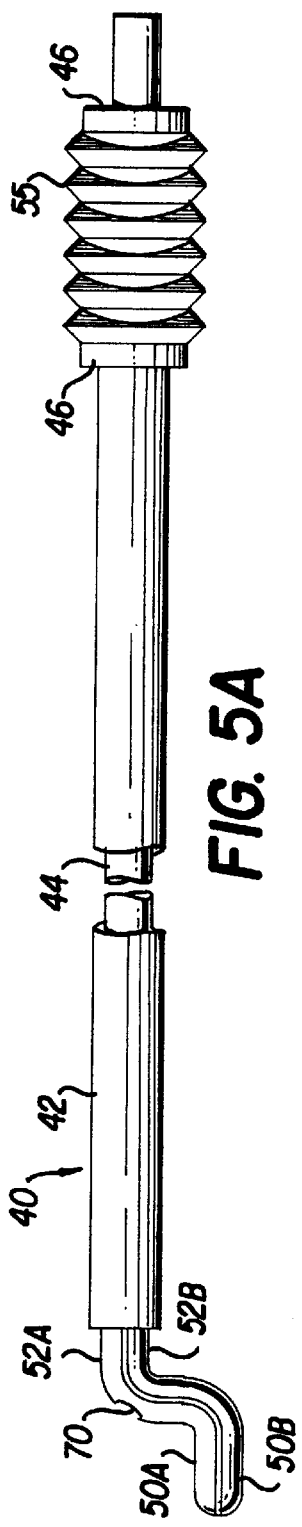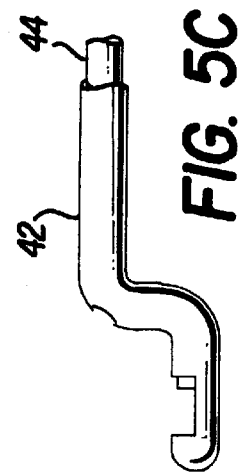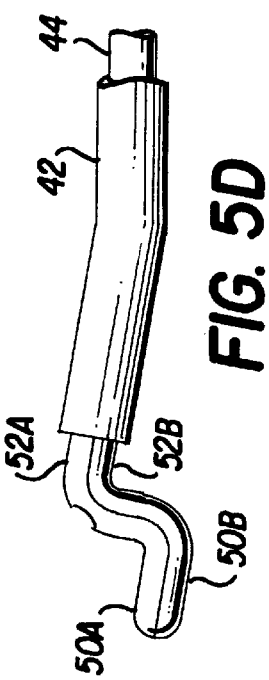

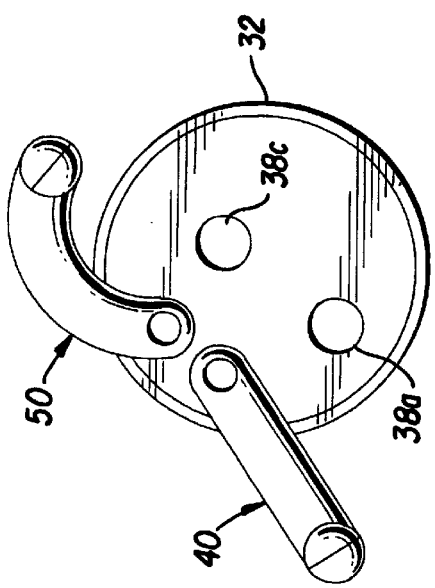
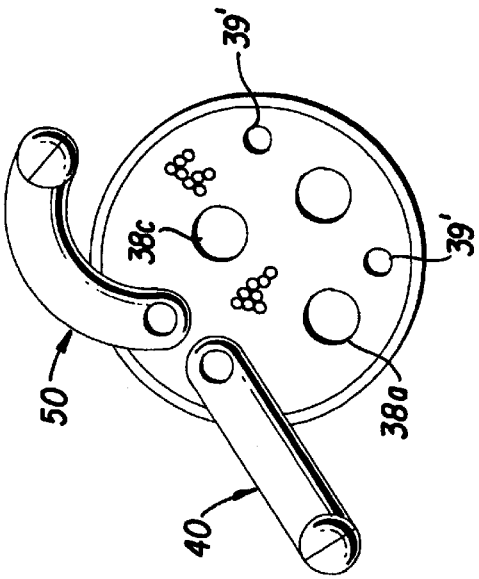
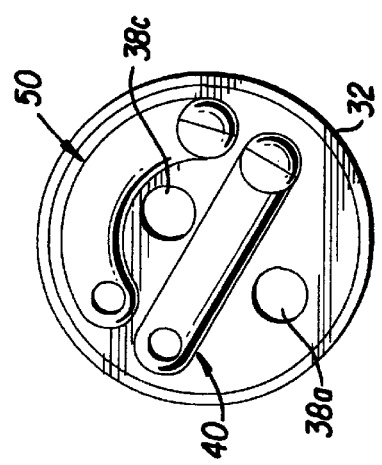
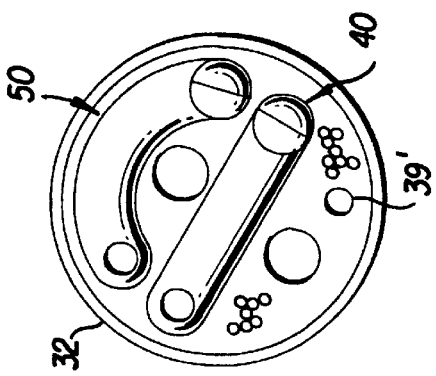

US 6,214,028 B1

SURGICAL INSTRUMENT WITH MULTIPLE ROTATABLY MOUNTED OFFSET END EFFECTORS AND METHOD OF USING THE SAME

RELATED PATENT APPLICATION DATA

This is a divisional of application Ser. No. 08/847,189 filed May 1, 1997, now U.S. Pat. No. 6,017,358. The entire disclosure of the prior application is hereby incorporated by reference herein in its entirety.

This application is related to applicant's copending applications Ser. No. 08/366,285 filed on Dec. 29, 1994, now U.S. Pat. No. 5,665,109; Ser. No. 08/377,723 filed on Jan. 25, 1995, now U.S. Pat. No. 5,643,295; Ser. No. 08/401,002 filed Mar. 9, 1995, now U.S. Pat. No. 5,695,505; Ser. No. 08/585,875 filed Jan. 16, 1996, now U.S. Pat. No. 5,810,853; and Ser. No. 08/758,648 filed Nov. 27, 1996, now U.S. Pat. No. 5,759,188; the disclosures of which are incorporated herein by reference. Also, this application is related to applicant's concurrently filed applications entitled "Surgical Instrument with Rotatably Mounted Offset End Effector and Method of Using the Same", "Suturing Instrument with Rotatably Mounted Offset Needle Holder and Method of Using the Same", and "Suturing Instrument with Multiple Rotatably Mounted Offset Needle Holders and Method of Using the Same", the disclosures of which are also incorporated herein by reference.

BACKGROUND OF THE INVENTION

1. Field of the Invention

The present invention pertains to surgical procedures conducted on bodily or anatomical tissue and, more particularly, to an apparatus and method for accomplishing various procedures during endoscopic and open surgery.

2. Discussion of the Related Art

Various steps are accomplished in both open surgery and endoscopic surgery. Generally the multiple steps require various operating instruments, or "end effectors". "Open surgery" refers to surgery wherein the surgeon gains access to the surgical site by a relatively large incision and "endoscopic surgery" refers to minimally invasive surgery wherein the surgeon gains access to the surgical site via one or more portals through which endoscopes are introduced to view the surgical site and through which instruments having end effectors, such as forceps, cutters, needle holders, cauterizers, clip applicators, and the like, are introduced to the surgical site.

The performance of an endoscopic procedure typically involves creation of one or more puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, scissors, forceps, needle holders and the like into the anatomical cavity.

The various end effectors at the distal end of the instrument are manipulated by the surgeon using controls disposed at the proximal end of the instrument. Of course, it is desirable to move the end effectors through various paths, depending on the step being performed. Traditionally, this was accomplished by moving the entire distal end of the endoscopic instrument. However, recently it has been proposed to provide a plurality of end effectors on a single endoscopic instrument to minimize the number of puncture sites and thus reduce the risk and healing time associated with endoscopic surgery. For example, copending U.S. application Ser. No. 08/758,648 filed Nov. 27, 1996, the disclosure of which is incorporated herein by reference discloses a device having two needle holders for suturing.

When a plurality of end effectors are incorporated into a single endoscopic device it is often desirable to move the end effectors individually with respect to one another without necessarily moving the entire distal end of the device. Also, it is often desirable to move the end effector through a predetermined path, such as an arc or the like, to manipulate tissue without repositioning the entire endoscopic device.

Of course, it is also generally desirable to minimize the size of each puncture site. Further, in order to permit operations on a wide range of tissue sizes, it is desirable to provide a wide range of relative movement between the end effectors. These objectives, minimal number/small size punctures and wide range of relative movement, are seemingly contradictory. Conventional devices have not achieved the above-noted objectives.

U.S. Pat. No. 5,582,617 discloses an endoscopic instrument having an end effector that can move from a position within the diameter of the barrel of the device to a position outside the diameter. However, this device must pivot about an axis that is transverse to the axis of the barrel and an axis that is coincident with the axis of the barrel and thus requires a complex movement and linkage to accomplish the disclosed functions. Accordingly, this device falls short of providing an end effector that can be utilized over a large working span for a wide range of applications.

SUMMARY OF THE INVENTION

Accordingly, it is a primary object of the present invention to overcome the above-mentioned disadvantages of the prior art and to improve surgical instruments and methods of surgery including endoscopic surgery.

It is also an object of the invention to increase the working span and minimize the insertion diameter of a surgical instrument.

Yet another object of the present invention is to minimize the number of puncture sites required for performing operative steps on anatomical tissue in an endoscopic or open surgery procedure by inserting more than one end effector through a single puncture site or incision with an instrument that is operable to move the end effectors relative to one another in a cooperative manner to operate on anatomical tissue.

A first aspect of the present invention is generally characterized in an instrument for operating on anatomical tissue including a barrel, at least two shafts extending through the barrel and at least one end effector mounted on each shaft. The end effectors are offset from the axis of the shaft by a connecting member to permit the end effector to rotate through a path that is outside of the diametrical dimension of the barrel. During insertion, the end effectors can be positioned within a diametrical dimension of the device either by rotating the shaft or by drawing the shaft and the end effectors into the barrel in an axial manner.

In another aspect of the invention, the end effectors are manipulated relative to one another in concert to facilitate tissue manipulation, ligating, cutting, clipping cauterizing or similar operations.

Other objects and advantages of the present invention will become apparent from the following description of the

BRIEF DESCRIPTION OF THE DRAWINGS

FIG. 5A is a side view of a driver of the first preferred embodiment;

FIG. 5B illustrates an alternative driver;

FIG. 5C illustrates an alternative driver;

FIG. 5D illustrates an alternative driver;

FIGS. 15A and 15B illustrate a sixth preferred embodiment;

FIGS. 16A and 16B illustrate a seventh preferred embodiment;

DETAILED DESCRIPTION OF THE PREFERRED EMBODIMENTS

The instrument of the present invention can be utilized for any type of anatomical tissue in any type of anatomical cavity. Accordingly, while the instrument is described hereinafter for use with a portal sleeve in endoscopic procedures, such as laparoscopy, the instrument can be used in open surgery and with catheters and other small and large diameter tubular or hollow cylindrical members providing access to small cavities, such as veins and arteries, as well as large cavities, such as the abdomen.

Figure 1:
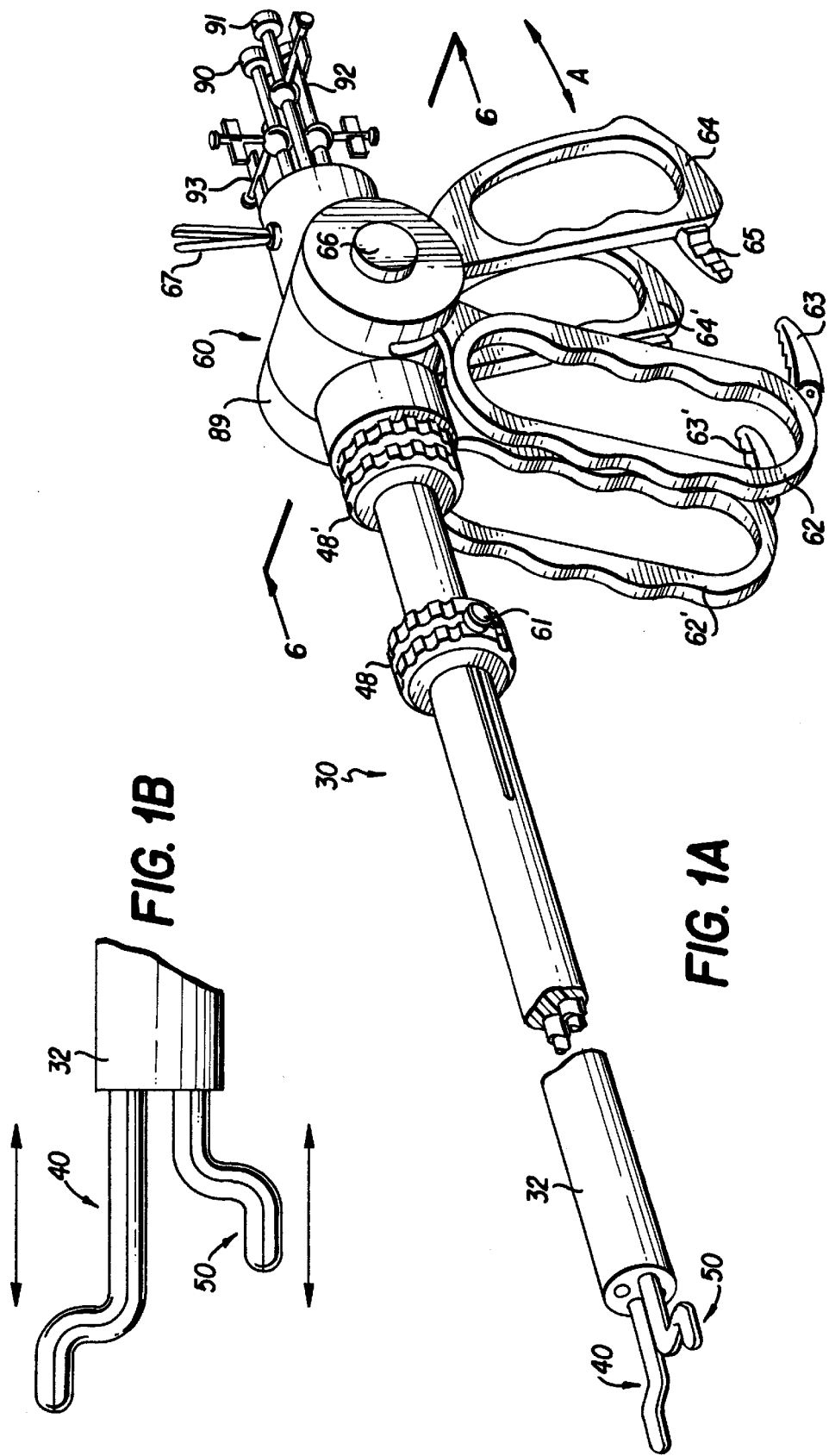
FIG. 1A illustrates the suturing instrument of the first preferred embodiment.
FIG. 1B illustrates distal/proximal movement of the driver.

A surgical instrument according to a first preferred embodiment of the present invention is illustrated at 30 in FIG. 1A and includes cylindrical barrel, or outer shaft, 32 which has an elongated passage defined therein, driver 40, and driver 50. Driver 40 and driver 50 are substantially contained within cylindrical barrel 32 as is described in detail below.

Figure 2:
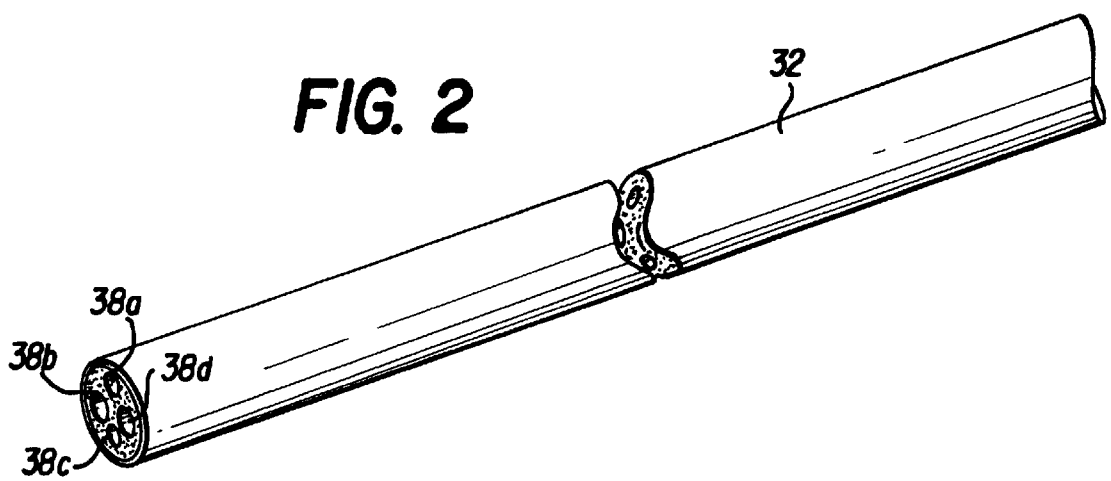
FIG. 2 is a perspective view of the barrel of the first preferred embodiment.

As shown in FIGS. 1A and 2, barrel 32 terminates distally at a distal end which is disposed within the body cavity of a patient during use and terminates proximally at a proximal end which is disposed externally of the patient during use. As shown in FIG. 2, barrel 32 includes a plurality of operating channels 38a–d extending longitudinally therethrough. Barrel 32 can have additional channels for receiving one or more additional instruments to be introduced in the abdominal cavity or barrel 32 can have fewer channels as needed. Optical fibers 39 extend through barrel 32 to transmit light from a proximal light source to the body cavity of a patient. Channels 38a–d can be formed by thin wall, tubular sleeves extending longitudinally through barrel 32 or merely by void spaces defined by optical fibers 39. FIG. 1B illustrates that driver 40 and driver 50 can be movable in proximal and distal directions.

FIG. 5A illustrates driver 40 removed from barrel 32 for illustrative purposes. Driver 40 includes elongated, tubular outer member 42 and elongated tubular inner member 44 disposed within outer member 42. Outer member 42 and inner member 24 define a shaft that is rotatable in barrel 32. Outer member 42 has a distal end on which two diametrically enlarged flanges 46 are disposed. Flanges 46 serve to fix collar 55, which has circumferential teeth, on outer member 42 while permitting collar 55 to rotate with respect to outer member 42. The function of collar 55 is described in detail below.

FIG. 5B illustrates driver 40 having pivoting jaws 50A and 50B. FIG. 5C illustrates driver 40 having flexible inner member 44 which can be advanced distally to grasp a needle or other object disposed in a notch formed in outer member 42. FIG. 5D illustrates driver 40 that is flexible and can be drawn into barrel 32 to be straightened. In a normal state driver 40 of FIG. 5D is angled.

The end effectors of this embodiment are forceps and are constituted of jaw members 50A and 50B biased to be normally disposed in an open position in which there is a gap defined between jaw members 50A and 50B. Of course, the inner surfaces of jaw members 50A and 50B can be shaped in any other appropriate way to firmly grasp tissue or other objects when jaw members 50A and 50B are in a closed position as shown in FIGS. 3A, 3B, 4, and 5. The end effectors can be of any other type including, but not limited to, cauterizing electrodes, clip applicators, scissors, needles, biopsy devices, or the like.

Driver 40 can be designed in various known ways permitting jaw members 50A and 50B to be movable between the closed position and the open position, such as the configurations disclosed above. Jaw members 50A and 50B can be biased toward the open position. Arms 51A and 51B serve as connecting members between jaw members 50A and 50B and inner member 44 and can be made entirely or partly of resilient, flexible or spring materials, or materials having shape memory, to be resiliently biased toward the open position while being movable to the closed position and back to the open position. Flanges 52A and 52B are respectively formed on arms 51A and 51B. Driver 50 is similar to driver 40 and similar elements thereof are designated with like reference numerals having the suffix "'". The opening and closing movement of jaw members 50A and 50B in this preferred embodiment is described below.

As illustrated in FIG. 1A, the proximal controls of the preferred embodiment include two sets of scissor type handles 62 and 64 and 62' and 64', extending from housing 89, that can be pivoted towards one another to cause movement of the associated end effector, in this embodiment jaw members 50A and 50B and jaw members 50A' and 50B', respectively. One set of handles is disposed on one side of barrel 32 and the other set of handles is disposed on the other side of barrel 32. The operation of one set of handles 62 and 64 is discussed in detail below with respect to driver 40. However, the other set of handlers 62' and 64' operate in connection with driver 50 in a similar manner.

Figure 6:
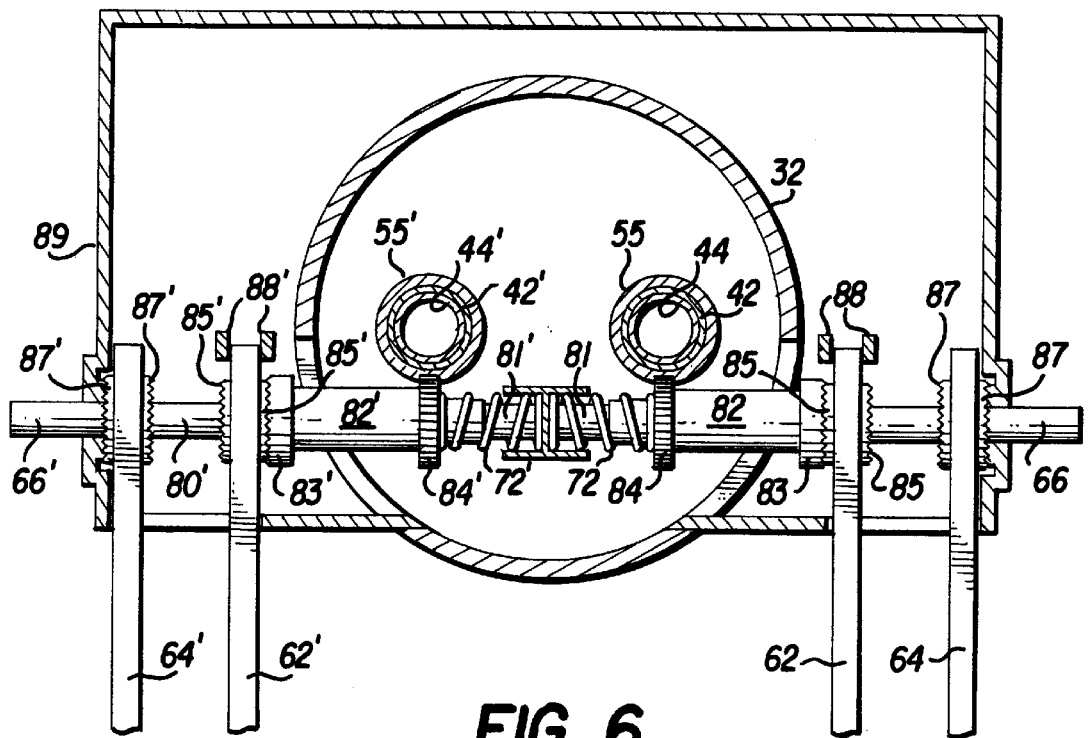
FIG. 6 is a sectional view of the inner mechanism of the proximal controls in an operative position taken along line 6—6 in FIG. 1.
Figure 7:
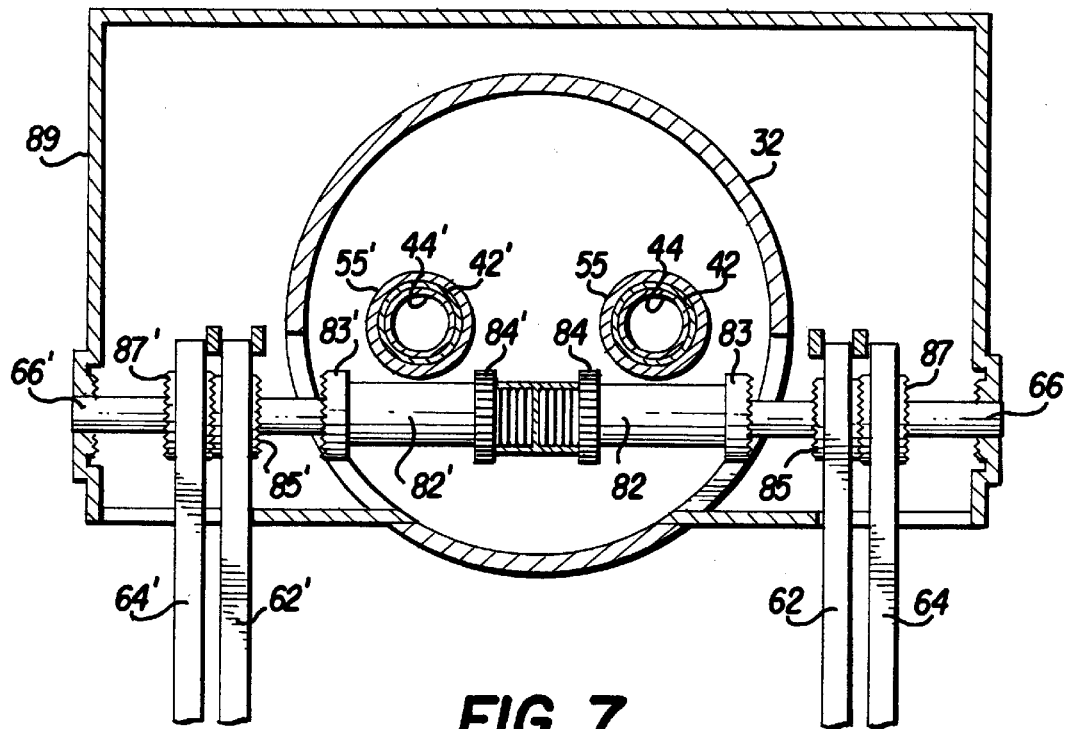
FIG. 7 is a sectional view of the inner mechanism of the proximal controls in an adjusting position taken along line 6—6 in FIG. 1.

Button 66 is provided proximate an axis of rotation of handles 62 and 64. Depressing button 66 disengages handles 62 and 64 from driver 40 and permits handles 62 and 64 to be rotated in concert about the axis of rotation as indicated by arrow A in FIG. 1A. This allows the surgeon to orient handles 62 and 64 in a desired manner during surgery. FIGS. 6 and 7 illustrate the internal mechanism coupling handles 62 and 64 to driver 40 and handles 62' and 64' to driver 50. Operating member 82 is rotatably disposed on shaft 140 and has gear portion 84 that is engaged with collar 55 on outer member 42 of driver 40. Operating member 82 is fixed axially on shaft 80 and has radially extending serrated teeth 83 formed on a side opposite gear portion 84.

Handle 62 is also rotatably mounted on shaft 80 and is slidable relative to shaft 80. Handle 62 is fixed in axial position by projections 88 formed on an inner surface of housing 89. Handle 62 has serrated teeth 85 on each side thereof at a top portion that is disposed around shaft 80. Shaft 80 is mounted on stem 81 and is normally biased to the right in FIG. 6 by spring 72 to press serrated teeth 83 into engagement with serrated teeth 85 thus fixing the relative position of operating member 82 and handle 62. Handle 64 is rotatably mounted on shaft 80 and fixed axially on shaft 80. Serrated teeth 87 are formed on each side of handle 64 at a top portion that surrounds shaft 80 and serrated teeth 87 are normally biased by spring 72 into engagement with teeth formed on an inner surface of housing 89 to fix the position of handle 64 with respect to barrel 34. In this state handle 62 is coupled to outer member 42 of driver 40 and handle 64 is fixed in position. Pressing handle 62 towards handle 64 will cause outer member 42 to move over flanges 52A and 52B (see FIG. 5) to close jaws 50A and 50B.

When shaft 80 is pressed to the left in FIG. 6, by depressing button 66, serrated teeth 87 engage serrated teeth 85 to fix the relative positions of handles 62 and 64 and serrated teeth 83 are disengaged from serrated teeth 85 to disengage handle 62 from driver 40, as illustrated in FIG. 7. This permits the set of handles 62 and 64 to be rotated in concert to the desired orientation. Button 66' is also illustrated as being depressed in FIG. 7 to illustrate the motion of the mechanism associated with driver 50.

As noted above, cam surfaces 52A and 52B are formed on outer surfaces of arms 51A and 51B respectively. When handle 62 pressed towards handle 64, outer member 42 moves distally over cam surfaces 52A and 52B causing jaw members 50A and 50B to move toward one another to the closed position. Cam surfaces 52A and 52B can be formed by bent portions defined in legs 51A and 52B or by separate elements that are attached to, or formed on, legs 51A and 51B. Release of handles 62 and 64 causes jaw members 50A and 50B to return to the open position due to the resilient bias of arms 51A and 51B. Lock protrusions 63 and 65 are disposed on handles 62 and 64 respectively (see FIG. 1A) and are serrated to interlock and allow the position of handles 62 and 64 to be maintained in a state corresponding to a desired position of jaw members 50A and 50B. Lock protrusions 63 and 65 can be pivoted to a position of which they will not interlock if desired. Additionally, handles 62 and 64 can be biased apart or outer member 44 can be biased distally or proximally, depending on desired operating characteristics.

Driver 50 is constructed similarly to driver 40 and thus further detailed description thereof is omitted. It will be appreciated that the jaw members or other end effector of driver 40 and driver 50 can be of different configurations dependent upon procedural use and other considerations such as cost. Also, cutting elements 53 can be provided on the jaw members as needed to cut suture material or tissue (see FIG. 4). The second set of handles 62' and 64' can be coupled to driver 50 in a similar manner. Accordingly, control of driver 50 is similar to that of driver 40 and further detailed description is omitted. Also, housing 89 and 89' can be positioned along a central transverse axis of barrel 32 and can be rotatable. In such a case an offset gear arrangement can be provided to couple handle 62 to collar 55.

Figure 8:
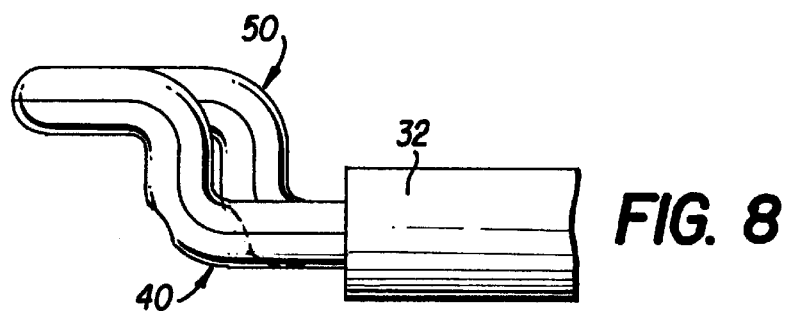
FIG. 8 is a side view of the distal end of the first preferred embodiment.

The shafts of driver 40 and driver 50 are disposed in channels 34b and 34d respectively to extend through barrel 32 and can be rotated about their respective longitudinal axes relative to barrel 32 by rotating knob 48 (for driver 40) or knob 48' (for driver 50). Push buttons 61 and 63 are respectively provided for unlocking knobs 48 and 48'. Also, arms 51A and 51B of needle driver 40 can be positioned to extend beyond arms 51A' and 51B' of driver 50, i.e. the transverse portion of the arms are in different planes, as illustrated in FIG. 8, to permit the arms to be placed in an overlapped crossed position (illustrated in FIGS. 3A and 3B). As noted above, driver 40 and driver 50 can be movable proximally and distally.

Channel 34a and channel 34b can be used as operating channels for suction devices, irrigation devices, or any other appropriate instrument such as a cautery device or the like. Also, aperture 70 is formed in a position of arm 51B that is proximal a distal end of inner member 44 to define an operating channel through driver 40 and aperture 70' is formed in arm 51B' to define an operating channel through driver 50 (See FIG. 3B for example).

Figure 3A:
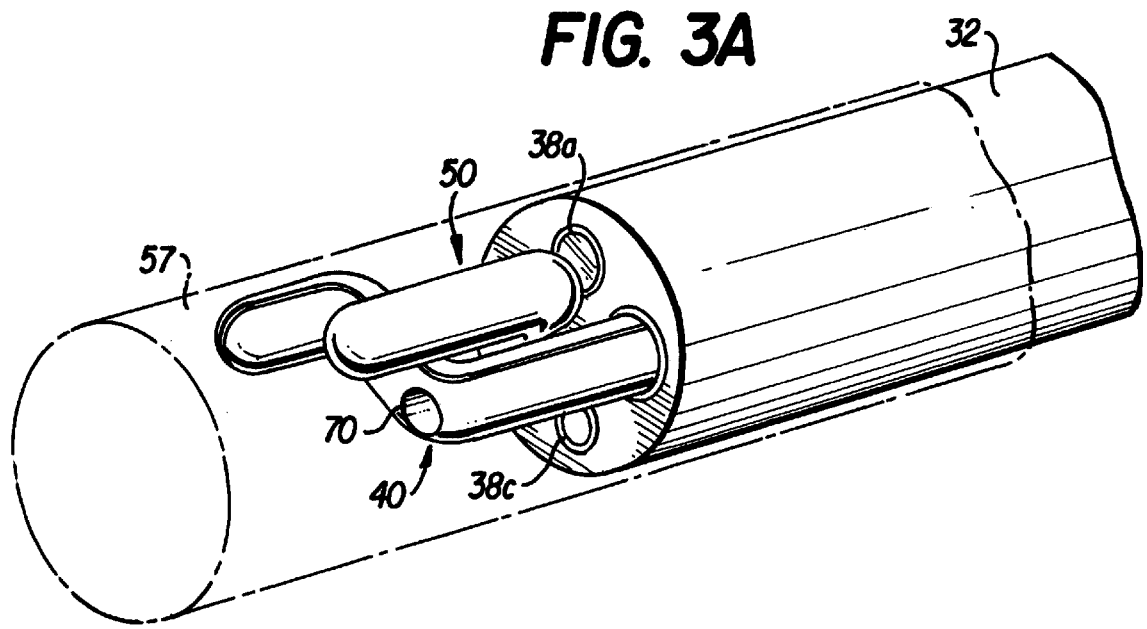
FIG. 3A is a perspective view of the distal end of the first preferred embodiment in the insertion position.
Figure 3B:
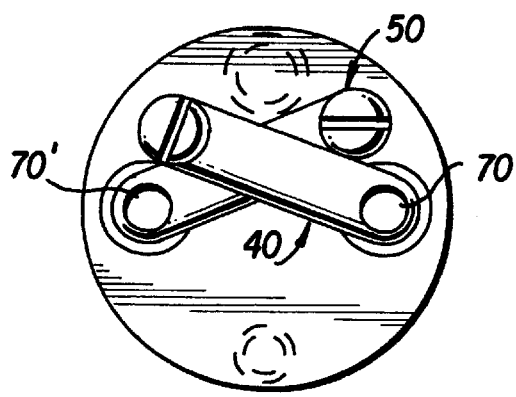
FIG. 3B is an end view of the distal end of the first preferred embodiment in the insertion position.
Figure 4:
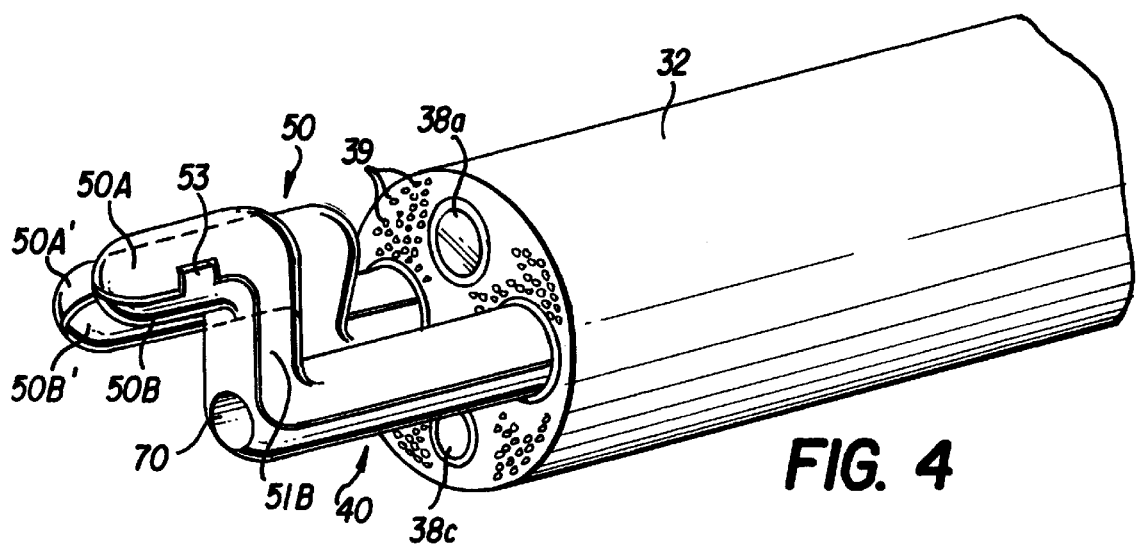
FIG. 4 is a perspective view of the distal end of the first preferred embodiment in an operative position.

In use, instrument 30 is inserted into a body cavity using known techniques, while driver 40 and driver 50 are in the position illustrated in FIGS. 3A and 3B. Note that the entire device can be inserted through a single puncture site. Also, in this position, jaw members 50A and 50B and 50A' and 50B', or any other appropriate end effectors, are disposed within the diametrical dimension of barrel 32 because the respective arms are crossed over one another. By grasping proximal controls 60, the distal end of suturing instrument 30 is guided to the operative site through a portal sleeve positioned in the wall of an anatomical cavity. The portal sleeve can be positioned in the anatomical cavity wall using any suitable penetrating technique, including those creating puncture sites by means of removable obturators, such as trocars, and can include a valve housing, if desired, to prevent loss of pneumoperitoneum during insertion and withdrawal of the instrument. Further, retractable sheath 57, which is illustrated in phantom in FIG. 3A, (or another appropriate device) can be provided to facilitate insertion through a portal sleeve valve by protecting driver 50 and driver 40. Visualization of the endoscopic procedure can be accomplished using a conventional endoscope incorporated into operating channel 38a, for example (known as a single puncture procedure) or separately positioned within the anatomical cavity through a second portal sleeve located at another puncture site (known as a double puncture procedure).

Prior to insertion, buttons 66 and 66' are pushed to the position illustrated in FIG. 7 to permit the orientation of the handle sets to be adjusted as desired. After adjustment, buttons 66 and 66' are released and handles 62 and 64 are set in a desired relative position by the surgeon so that jaw members 50A and 50B of driver 40 are in the desired position. Lock protrusions 63 and 65 can maintain handles 62 and 64 in the closed or partially closed state to permit an object to be securely held while freeing the surgeon's hands for other manipulation.

At any point during the operative procedure, channel 38c can be used for irrigation or aspiration, can serve as a space for holding suture material, a needle, clips or the like or can be used as a portal for the introduction of other medical instruments such as, forceps, cutting members, ligators, or cautery devices. Also, channels 38b and 38d can be used for irrigation, aspiration, insertion of an instrument or the like by utilizing the passage through inner member 44/44' of driver 40 and/or driver 50. Tissue can be manipulated, cut, or the like, by manipulating handles 62, 64, 62', and 64' as well as knobs 48 and 48' in the desired manner. Also, barrel 32 can be rotated to move the end effectors From the above, it will be appreciated that the instrument according to the present invention permits manipulation of anatomical tissue during endoscopic procedures without the need for multiple instruments inserted through multiple puncture sites. Driver 40 and driver 50 each are operable to move an end effector to manipulate or operate on anatomical tissue positioned proximate driver 40 and driver 50, and can be moved through a large working span. While the end effectors described above are forceps jaws, it will be understood that any end effectors can be used. Also, any end effectors, including the forceps jaws, can be used as a cautery electrode by coupling an electrical power source to the end effector through electrical connector 67, 67' or 81 (which is illustrated in phantom).

Figure 9:
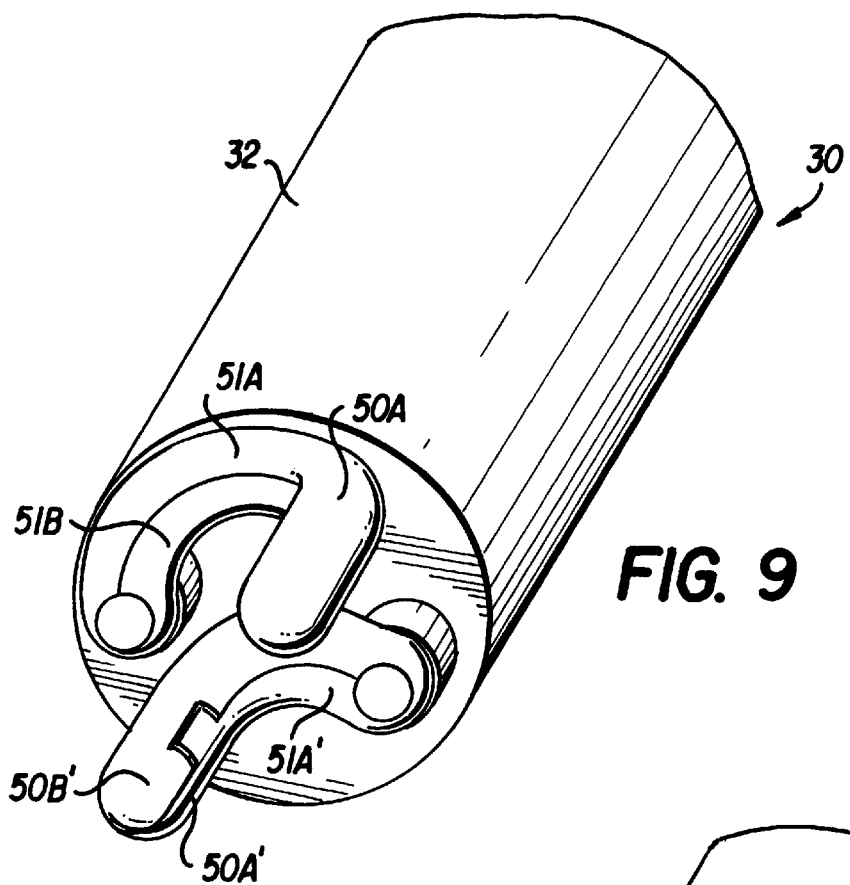
FIG. 9 is a perspective view of the distal end of the second preferred embodiment in the insertion position.
Figure 10:
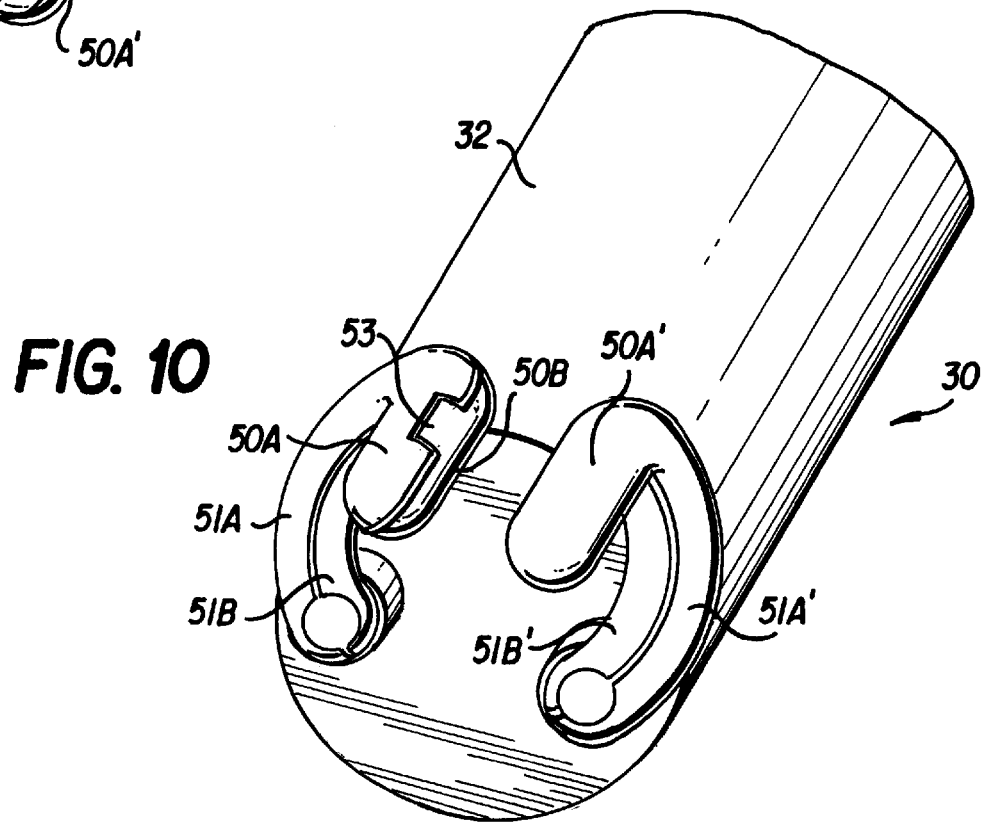
FIG. 10 is a perspective view of the distal end of the second preferred embodiment in an operative position.

A surgical instrument according to a second preferred embodiment is illustrated at 30 in FIGS. 9 and 10. The second preferred embodiment includes driver 40 and driver 50 and is similar to the first preferred embodiment except for the configuration of arms 51A, 51B, 51A' and 51B' which are curved. Jaw members 50A, 50B and 50A' and 50B' are moveably mounted on a distal end of a respective arm to open and close in a manner similar to the jaws described above.

As is best illustrated in FIG. 9, the arms can easily be confined within the diametrical dimension of barrel 32 during insertion. During a procedure the arms can be moved, by rotating knobs 48 and 48' to cause the jaw members, or any other appropriate end effector, to be moved through a path that is outside of the diametrical dimension of barrel 32. This embodiment can be used to manipulate tissue in a manner similar to the first embodiment. However, the insertion position of this embodiment, in which the arms and jaw members are contained within the diametrical dimension of tubular member, does not require that the arms cross one another. Therefore, the arms need not be disposed in different planes. The jaw members and shafts of this embodiment can be manipulated in the same way as the first embodiment.

Figure 11B:
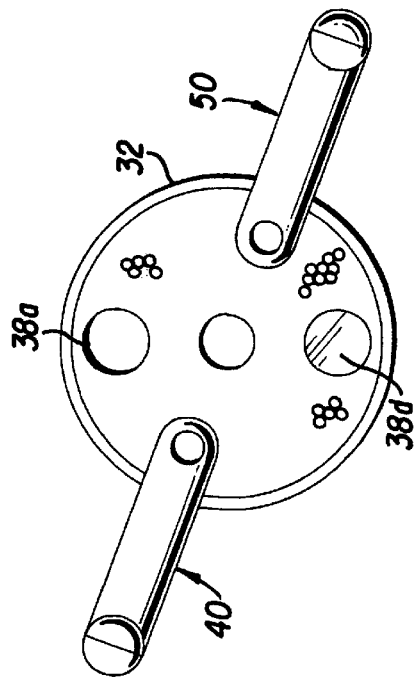
FIGS. 11A and 11B illustrate a second preferred embodiment.
Figure 11A:
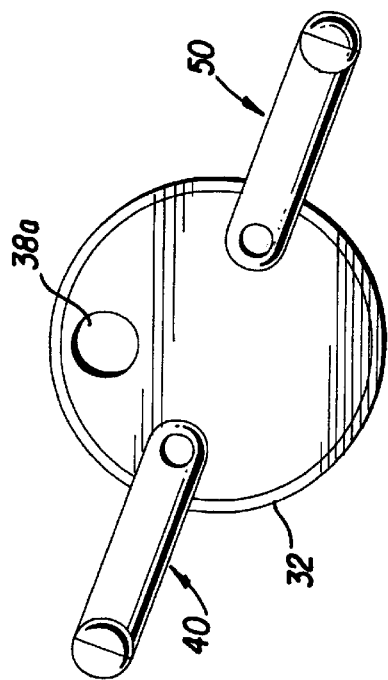
Figure 12B:
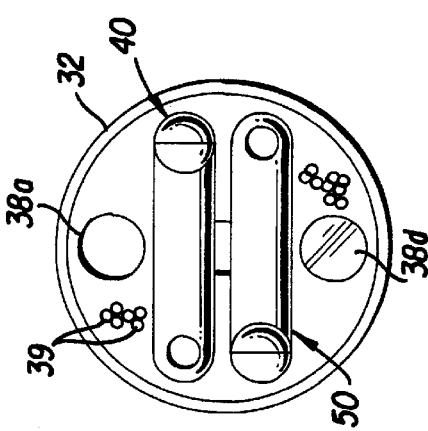
FIGS. 12A and 12B illustrate a third preferred embodiment.
Figure 12A:
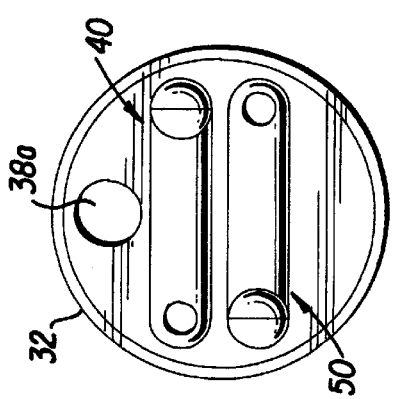

FIGS. 11A and 11B illustrate a third preferred embodiment. Shafts of driver 40 and driver 50 of the third preferred embodiment are offset from one another in both the horizontal and vertical direction as viewed in FIGS. 11A and 11B. Also, operating channel 38a is provided in barrel 32. In other respects, the third embodiment is similar to the first embodiment. FIGS. 12A and 12B illustrate a fourth embodiment that is similar to the third embodiment. However, the fourth embodiment is adopted for "single puncture" procedures. Specifically, operating channels 38a–e are defined in barrel 36. Shafts of drivers 40 and 50 are disposed in operating channels 38b and 38d respectively. Operating channels 38a, c, and e can be used for an optical endoscope for visualization and other instruments, such as a clip applicator or forceps, if necessary. Optical fibers 39 are dispersed throughout barrel 32 to direct light from a proximal light source into the body cavity.

Figure 13B:
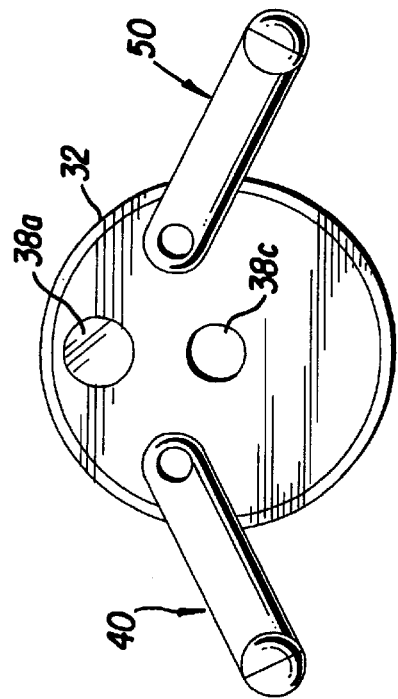
FIGS. 13A and 13B illustrate a fourth preferred embodiment.
Figure 14B:
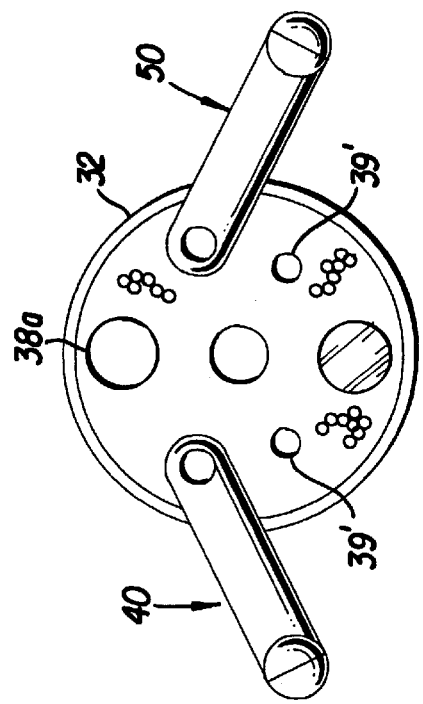
FIGS. 14A and 14B illustrate a fifth preferred embodiment.
Figure 13A:
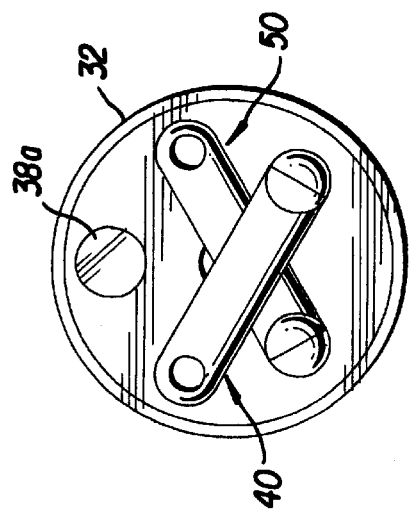
Figure 14A:
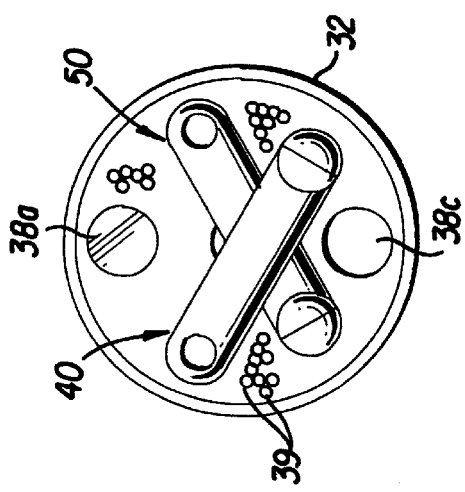

A fifth embodiment is illustrated in FIGS. 13A and 13B. In the fifth embodiment, the shafts of both drivers 40 and 50 are disposed in an upper half of barrel 32 as viewed in FIGS. 13A and 13B. Operating channels 38a and 38c are provided for the insertion of instruments or for irrigation or aspiration. The sixth embodiment illustrated in FIGS. 14A and 14B is similar to the fifth embodiment. However, in the sixth embodiment, an optical endoscope is disposed in operating channel 38a for viewing, operating channels 38c and 38e can accommodate instruments, such as a clip applicator or forceps, and light transmitting fibers 39 are provided for lighting the cavity. Alternatively fiber bundles 39', illustrated as dotted lines, can be provided instead of fibers 39 dispersed throughout the cross-sectional area of barrel 32.

In the seventh embodiment illustrated in FIGS. 15A and 15B the arm of driver 50 is curved and additional operating channels 38a and c are provided. In the eighth embodiment illustrated in FIGS. 16A and 16B, an optical endoscope is disposed in operating channel 38e and either distributed light fibers 39 or fiber bundles 39' are used for transmitting light.

Figure 17B:
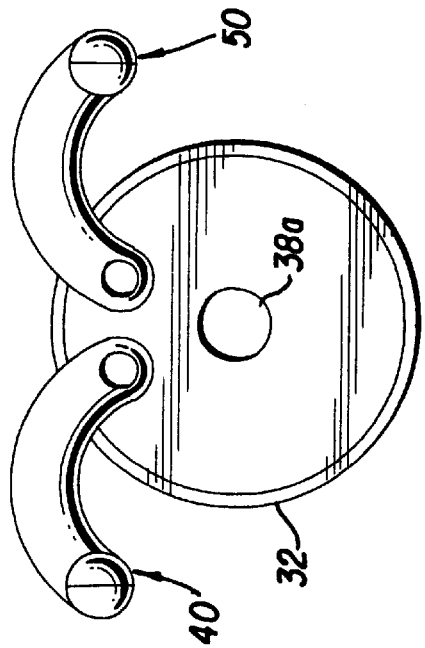
FIGS. 17A and 17B illustrate an eight preferred embodiment.
Figure 18B:
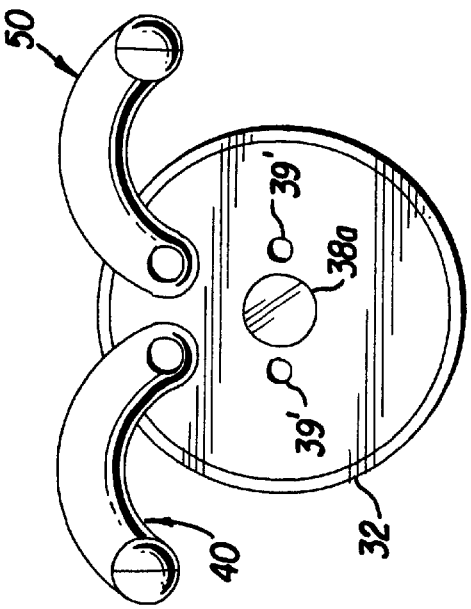
FIGS. 18A and 18B illustrate a ninth preferred embodiment.
Figure 17A:
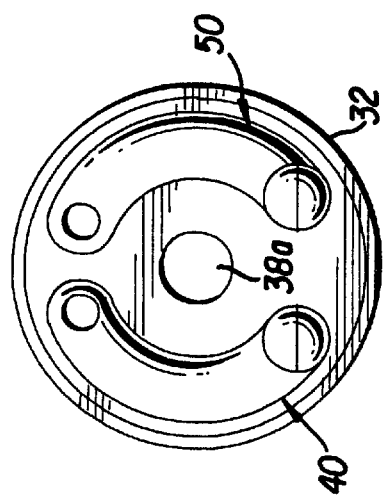
Figure 18A:
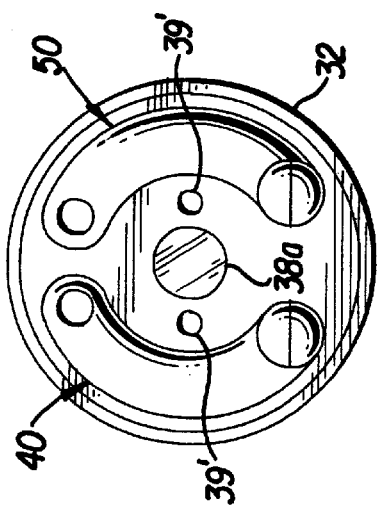

FIGS. 17A and 17B illustrate a ninth embodiment in which the arms of both driver 40 and driver 50 are curved and operating channel 38a is centralized for insertion of an instrument, for suction, aspiration, or the like. The tenth embodiment illustrated in FIGS. 18A and 18B is similar to the ninth embodiment but has optical endoscope in operating channel 38a for viewing and fiber bundles 39' for providing light. Of course this embodiment could have light fibers dispersed throughout the cross-sectional area of barrel 32 instead of fiber bundles 39'.

Figure 19B:
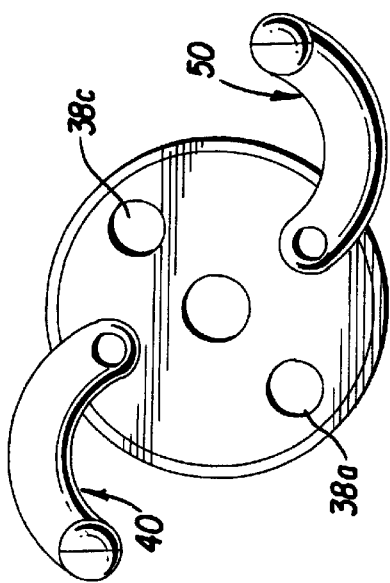
FIGS. 19A and 19B illustrate a tenth preferred embodiment.
Figure 19A:
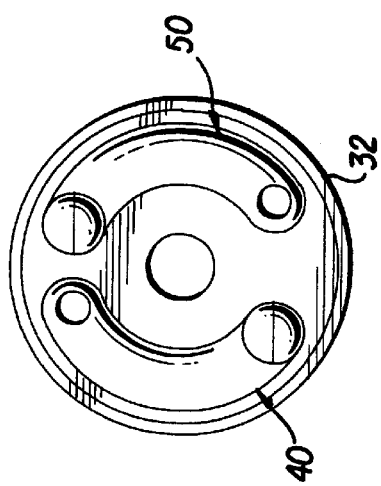

FIGS. 19A and 19B illustrate an eleventh embodiment with curved arms and operating channels 38a and 38c that are covered by the arms when driver 40 and driver 50 are in the insertion, or parked, position illustrated in FIG. 19A.

Figure 20B:
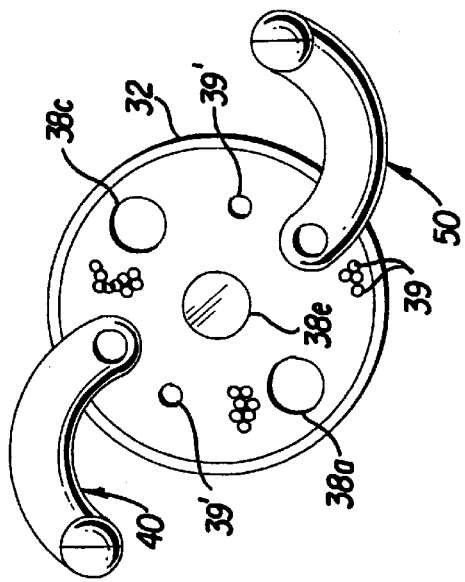
FIGS. 20A and 20B illustrate an eleventh preferred embodiment.
Figure 20A:
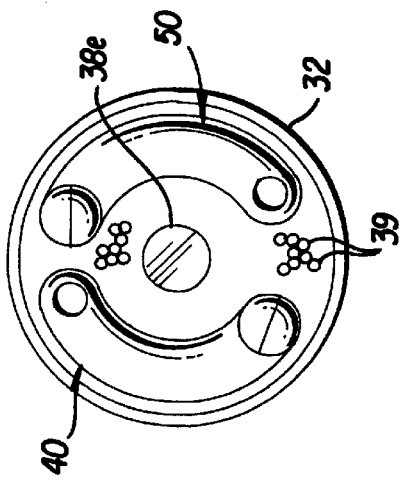

Centralized operating channel 38e is also provided. The twelfth embodiment illustrated in FIGS. 20A and 20B includes an optical endoscope in centralized operating channel 38e and light fibers 39 or fiber bundles 39'.

Figure 21:
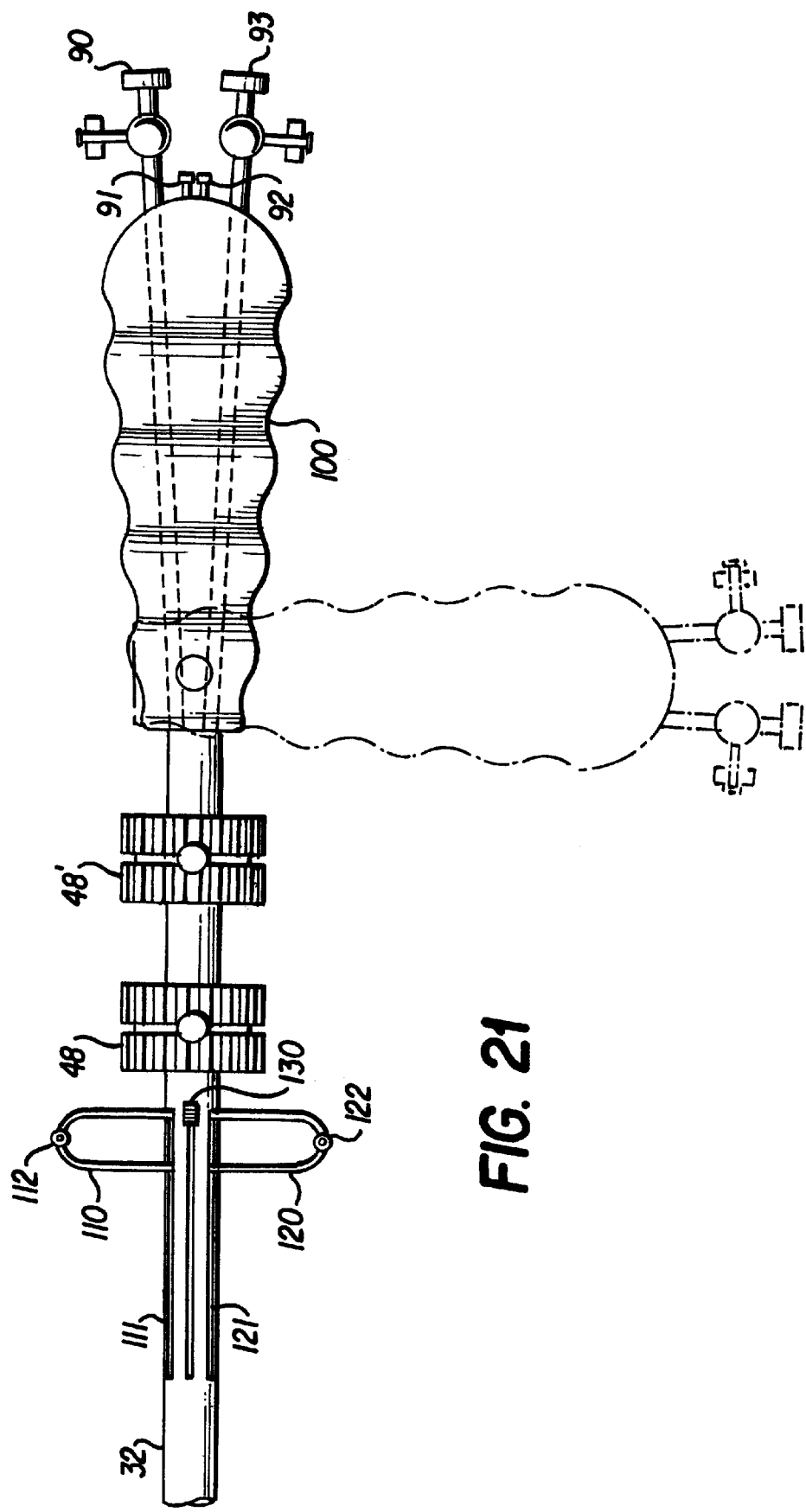
FIG. 21 illustrates an alternative arrangement of the proximal controls.

Any appropriate proximal controls, such as those disclosed above, can be used with the invention depending on the surgeon's preference and experience. FIG. 21 shows a modification of the proximal controls. Handle 100 is pivotally mounted to barrel 32 and can be locked in any desired position to facilitate manipulation, such as in the pistol grip position illustrated in phantom. U shaped handle 110, having ratcheting lock device 112, extends through a slot formed in barrel 32 and has one leg coupled to inner member 44 and one leg coupled to outer member 42. Compressing handle 110 thus moves outer member 42 distally with respect to inner member 44 to lock operate the end effector of driver 40. U-shaped handle 120, having ratcheting device 122, is coupled to driver 50 in a similar manner. Sliding handles 110 and 120 along respective slots 111 and 121 causes drivers 40 and 50 to move respectively in the proximal or distal direction. Sliding knob 330 is provided to permit movement of driver 40 and driver 50 in concert in the proximal and the distal directions. Knobs 48 and 48' can be rotated to rotate driver 40 and 50 respectively. Proximal apertures 90, 91, 92 and 93 are provided for the insertion of instruments into operating channels.

Figure 22:
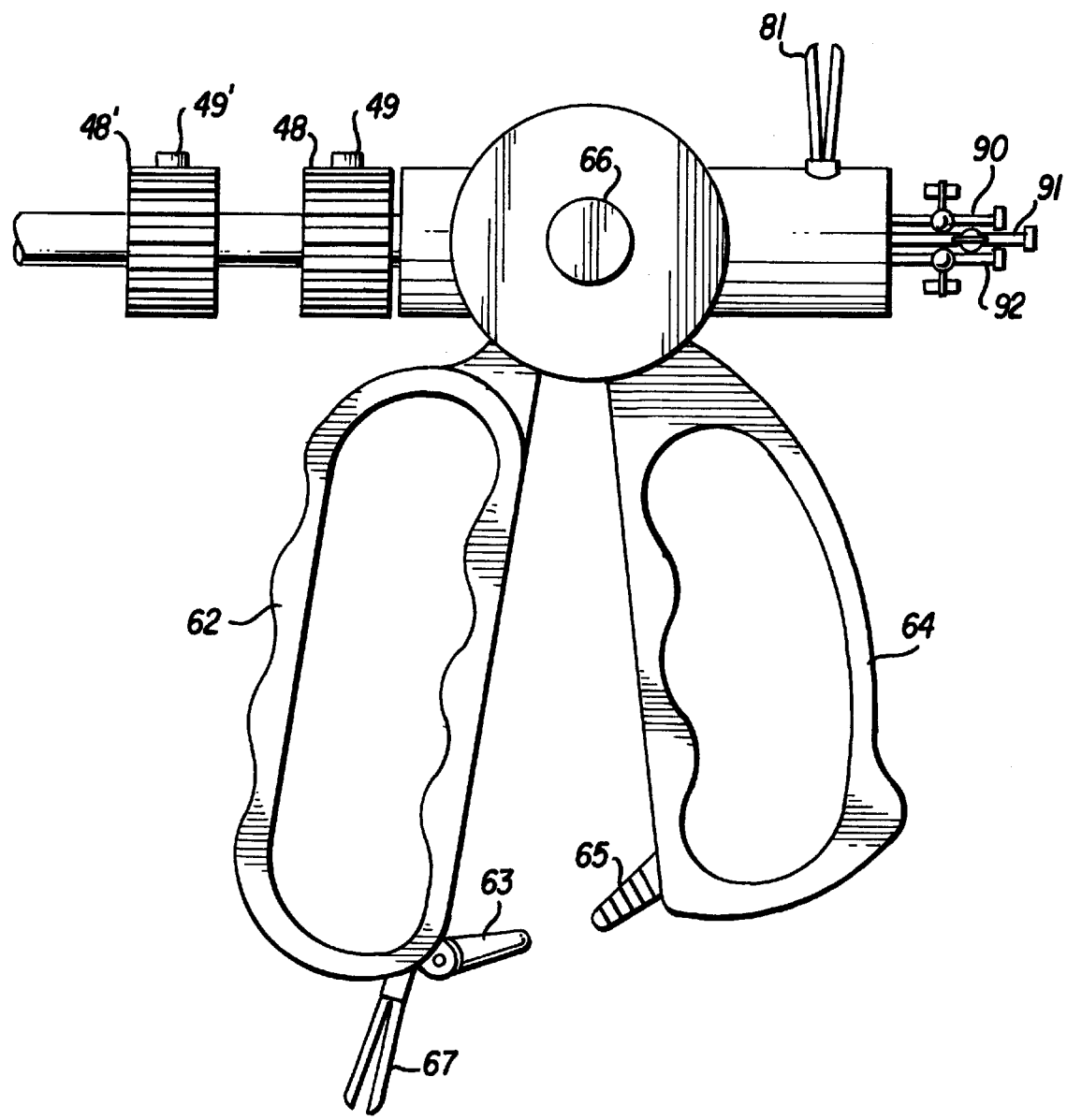
FIG. 22 illustrates another alternative arrangement of the proximal controls having only one set of handles.

FIG. 22 illustrates modified proximal controls 60 in which one set of handles 62 and 64 are selectively coupled to driver 40 or driver 50 for operating end effectors. Push button 66 is used to select either driver 40 or driver 50. Knobs 48 and 48' having locking push buttons 61, and 63 respectively are coupled to shafts of driver 40 and driver 50 to permit rotation and linear movement of driver 40 and apparatus 50.

Figure 23:
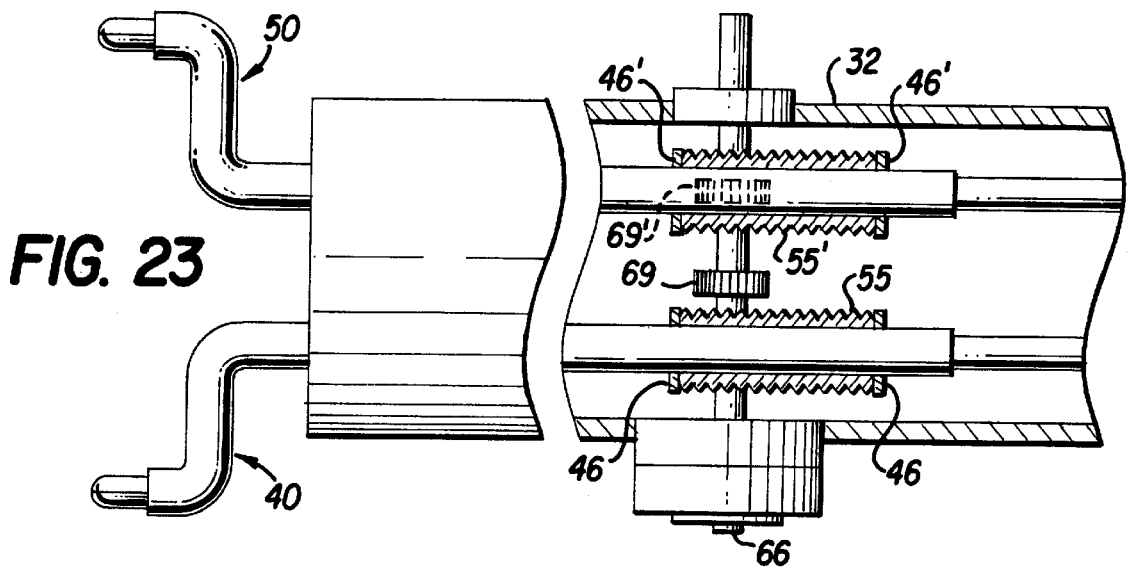
FIG. 23 illustrates the inner switching mechanism of the proximal controls of FIG. 22 in partial section taken along line 23—23.
Figure 24:
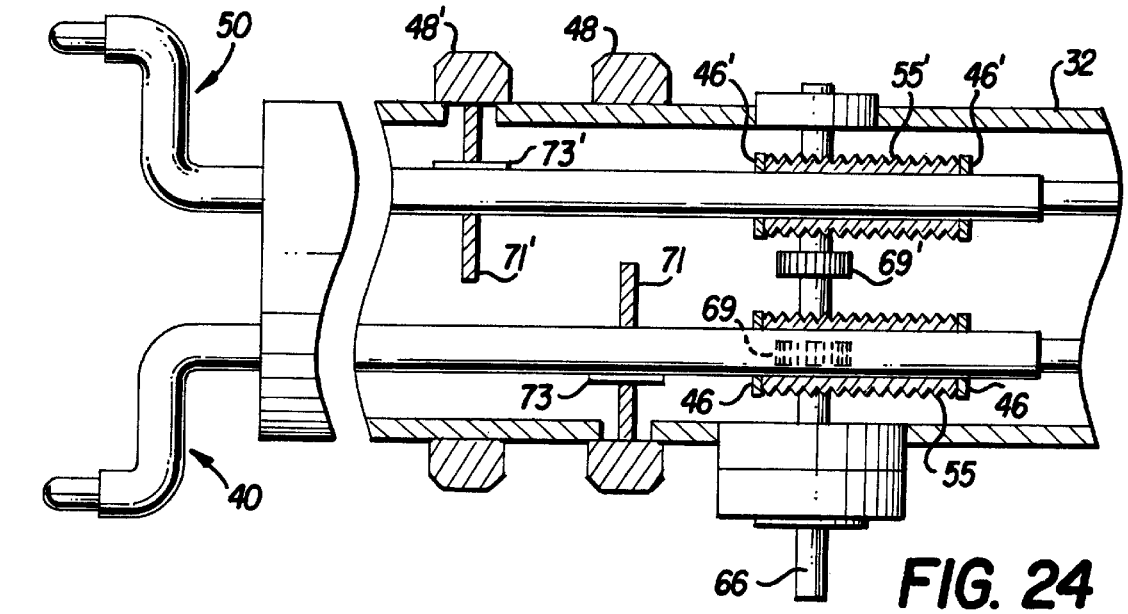
FIG. 24 illustrates the inner switching mechanism of the proximal controls of FIG. 22 in partial section taken along line 23—23.

FIGS. 23 and 24 illustrate the internal mechanism of the proximal controls illustrated in FIG. 22. Push button 66 is coupled to shaft 68 having gears 69 and 69' fixedly disposed thereon. In the position illustrated in FIG. 24, gear 69' is engaged with sleeve 55' of driver 50. Sleeve 55' is rotatably supported on outer member 42' of driver 55' by flanges 46'. Handles 62 and 64 are coupled to shaft 68 to rotate shaft 68 when handles 62 and 64 are pressed together, thus causing relative movement between inner member 42' and outer member 44' to operate an end effector of driver 50. Depression of push button 66 slides shaft 68 and causes gear 69 to engage with sleeve 55 of driver 40, as illustrated in FIG. 23, to operate an end effector of driver 40 in a similar manner. FIG. 24 also illustrates gears 71 and 71' that are respectively mounted on shafts of driver 40 and driver 50. Gears 71 and 71' can slide along the shafts but cannot turn with respect to the shafts because of keys 73 and 73' formed on the shafts and engaged in a keyway of the respective gears. Gears 71 and 71' are engaged respectively with teeth formed on inner surfaces of knobs 48 and 48'. Therefore, turning knobs 48 and 48' turns respectively the shafts of needle driver 40 and needle driver 50. This same turning mechanism can be used for the proximal controls illustrated in FIGS. 1 and 6. Also, the proximal control of FIGS. 22–24 can have variable orientation handles similar to those illustrated in FIGS. 1 and 6. Further, shaft 68 can be set to positions for disengaging both end effectors or for simultaneously operating both end effectors. Electrical connectors 67 and 81 are provided for unipolar or bipolar cauterization.

Figure 25:
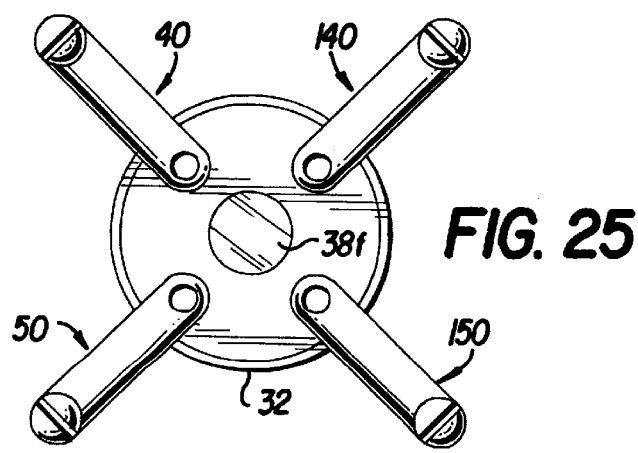
FIG. 25 illustrates a thirteenth embodiment of the invention having more than two driver.

Each of the preferred embodiments discussed above have two driver. However, the invention can include any appropriate number of driver for manipulating tissue or performing other procedures. FIG. 25 illustrates a thirteenth preferred embodiment having four driver. Specifically, driver 40, driver 140, driver, driver 50, and driver 150 are each rotatably mounted in an operating channel defined in barrel 32. Arms of the driver lie in different planes to permit the driver to be placed in an insertion position similar to the embodiments discussed above. The operating position illustrated permits tissue to be manipulated or other procedures to be accomplished. Of course, this embodiment can utilize any type of end effectors, as needed for the desired procedure. The thirteenth embodiment is particularly suited to dual electrode cauterization, clamping tissue between adjacent end effectors, or separating tissue by placing adjacent end effectors between tissue sections and moving the end effectors away from one another. Adjacent end effectors, acting as electrodes, can be pressed against opposing sides of tissue to cauterize the tissue. The polarity of each electrode can be changed to permit any two electrodes to be used in combination. An optical endoscope can be incorporated into central channel 38f. Also, additional channels can be provides as needed. Of course, this embodiment can utilize optical fibers or fiber bundles for transmitting light similar to the other embodiments. Other aspects of this embodiment are similar to the previous embodiments.

In each of the embodiments discussed above, two opposed jaws are moveable toward one another. However, one of the jaw members can be fixed and the other jaw member can be moveable. The driver can be made of flexible or shape memory materials and can be drawn entirely into the barrel as disclosed in applicant's copending application entitled "Surgical Instrument with Rotatably Mounted Offset End Effector and Method of Using the Same", the disclosure of which is incorporated herein by reference.

Figure 26:
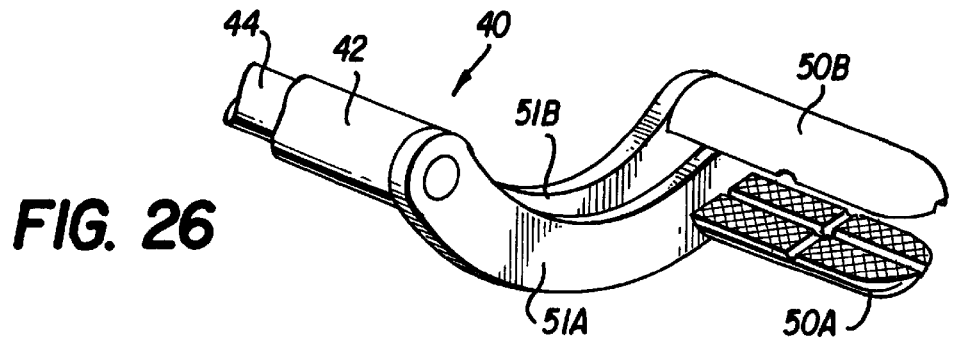
FIG. 26 illustrates the distal end of another alternative driver.

FIG. 26 illustrates an alternative driver 40 in which arm member 51A is coupled to inner member 44 and arm member 51B is coupled to outer member 42. Relative rotation between inner member 44 and outer member 42 cause jaws 50A and 50B to open/close. Rotation in concert causes the end effector 50 move. Also, longitudinal and transverse grooves are formed in the jaws to facilitate grasping of a needle or the like.

The two or more driver, can be of the same design or of different designs. For example, one can have forceps jaws as an end effector and one can have a clip applicator as an end effector. Therefore, the invention can be used for pickup and cutting, pickup and clipping, pickup and suture, or lysis of adhesion procedures. Also, any type of end effector can be used as a cautery electrode by being coupled to a proximal electric power source through electrical connector 67 (see FIG. 1A). Also, a button can be provided to selectively switch the electric power between end effectors for unipolar cauterization. For example, button 66 can be used.

The jaw closing mechanism of the driver shown and described herein are merely exemplary of the types of mechanisms that can be used according to the present invention. For example, the jaw members can pivot or slide relative to one another as disclosed in the related applications noted above and incorporated herein by reference. The jaw members can also carry cutting members, such as slots with sharp edges or protruding blades, and can have opposed arcuate or concave portions for clamping tubular objects, such as organs, without compressing the objects. Also, only one, or more than two driver can be provided. The mechanisms for moving the driver relative to one another and for operating end effectors are merely exemplary of the types of mechanisms that can be used to perform these functions and other mechanisms can be used.

Operation of the end effectors can be automatically controlled merely by squeezing the handles together as disclosed in the related applications incorporated herein by reference. For example, the handle can be coupled to one or more end effectors to accomplish a desired procedure merely by squeezing and releasing the handles. Squeezing the handles can perform pickup and cutting, pickup and clipping, pickup and stapling, lysis of adhesion, or any other desired procedure or combination of procedures.

The components of the surgical instrument of the present invention can be made of any suitable, medical grade materials to permit sterilization for reuse or disposal for single patient use. The components can be made of multiple parts of various configurations and materials to reduce cost. The invention can have various valves, stop-cocks and seals therein to control the flow of fluid and medical devices through the suturing instrument.

In as much as the present invention is subject to many variations, modifications and changes in detail, it is intended that all subject matter discussed above or shown in the accompanying drawings be interpreted as illustrative only and not be construed as limiting the scope of the invention which is defined by the appended claims.

What is claimed is:

1. A method of effecting a surgical procedure on anatomical tissue, said method comprising the steps of:

introducing first and second connecting members coupled to a distal end of a barrel of an endoscopic device into an area proximate the anatomical tissue, said barrel having a handle coupled to a proximal end of said barrel, said first connecting member including a first end effector extending therefrom, said first end effector having at least two relatively movable jaw members operable by said handle, said second connecting member having a second end effector extending therefrom, said second end effector having at least two relatively movable jaw members operable by said handle;

rotating said first connecting member about a first axis lying within said barrel from a first position within a diametrical dimension of said barrel into a second position in which at least an extending portion of said first end effector extends beyond the diametrical dimension of said barrel, said first end effector being offset from said first axis, whereby the movable jaw members, when closed, move out of the diametrical dimension of the barrel by the rotating alone; and manipulating said handle to operate said movable jaw members of said first and said second end effectors in order to move the first and second end effectors between a closed position and an open position whether the first end effector is contained entirely within the diametrical dimension of said barrel or the extending portion extends beyond the diametrical dimension of said barrel.

2. The method of claim 1, wherein, during said introducing step, said first connecting member and said second connecting member lie in different planes.

3. The method of claim 1, wherein said step of manipulating comprises rotating at least one of said first end effector and said second end effector.

4. The method of claim 1, wherein said step of manipulating comprises rotating said barrel.

5. The method of claim 1, wherein, during said introducing step, said first connecting member crosses said second connecting member and wherein said second end effector is contained entirely within a diametrical dimension of said barrel.

6. The method of claim 1, wherein at least one of said first end effector and said second end effector has a longitudinal axis that is offset from a longitudinal axis of said barrel.

7. The method of claim 1, wherein at least one of said first connecting member and said second connecting member extends transversely from said barrel.

8. The method of claim 1, wherein said first end effector has a longitudinal first effector axis that is offset from the first axis.

* * * * *